US011656180B2

(12) United States Patent
Flanagan et al.

(10) Patent No.: US 11,656,180 B2
(45) Date of Patent: May 23, 2023

(54) MULTI EXCITATION-MULTI EMISSION FLUOROMETER FOR MULTIPARAMETER WATER QUALITY MONITORING

(71) Applicant: YSI, Inc., Yellow Springs, OH (US)

(72) Inventors: Kevin R. Flanagan, Yellow Springs, OH (US); Christopher J. Palassis, Yellow Springs, OH (US)

(73) Assignee: YSI, INC., Yellow Springs, OH (US)

( * ) Notice: Subject to any disclaimer, the term of this patent is extended or adjusted under 35 U.S.C. 154(b) by 189 days.

(21) Appl. No.: 16/686,774

(22) Filed: Nov. 18, 2019

(65) Prior Publication Data

US 2020/0080941 A1    Mar. 12, 2020

Related U.S. Application Data

(63) Continuation of application No. 15/226,407, filed on Aug. 2, 2016, now abandoned.
(Continued)

(51) Int. Cl.
*G01N 21/64*    (2006.01)
*G01N 33/18*    (2006.01)

(52) U.S. Cl.
CPC ....... *G01N 21/6486* (2013.01); *G01N 21/645* (2013.01); *G01N 33/1826* (2013.01);
(Continued)

(58) Field of Classification Search
CPC ............. G01N 21/6486; G01N 21/645; G01N 33/1826; G01N 33/1886; G01N 2201/062; Y02A 20/20
See application file for complete search history.

(56) References Cited

U.S. PATENT DOCUMENTS 4,293,225 A    10/1981   Wheaton et al.
5,968,762 A    10/1999   Jadamec et al.
(Continued)

FOREIGN PATENT DOCUMENTS

CN    103245644 A        8/2013
CN    105004701 A   *   10/2015   ............. G01N 21/64
(Continued)

OTHER PUBLICATIONS

Nanjing University—CN 10500471 A—Google Patents English obtained Aug. 25, 2021 (Year: 2021).*
(Continued)

*Primary Examiner* — David P Porta
*Assistant Examiner* — Jeremy S Valentiner
(74) *Attorney, Agent, or Firm* — Ware, Fressola, Maguire & Barber LLP

(57) ABSTRACT

A fluorometer is provided for monitoring the quality of water, featuring an array of excitation sources, an array of multiple emission detectors and a signal processor. In the array of excitation sources, each excitation source provides respective excitation source optical signaling at a respective illuminating wavelength. The array of multiple emission detectors detects multiple emission wavelengths emitted from water containing information about multiple coexisting fluorescent species present in the water that emit optical radiation at at least two different wavelengths when illuminated by the respective illuminating wavelength provided from the array of excitation sources, and provide multiple emission detector signaling containing information about the multiple coexisting fluorescent species. The signal processor receives the multiple emission detector signaling, and determines corresponding signaling containing information about an identification of the multiple coexisting fluorescent species present in the water using a near-simultaneous
(Continued)

identification technique, based upon the multiple emission detector signaling received.

22 Claims, 4 Drawing Sheets

Related U.S. Application Data

(60) Provisional application No. 62/200,336, filed on Aug. 3, 2015.

(52) U.S. Cl.
CPC ... *G01N 33/1886* (2013.01); *G01N 2201/062* (2013.01); *Y02A 20/20* (2018.01)

(56) References Cited

U.S. PATENT DOCUMENTS

| | | | |
|---|---|---|---|
| 6,124,597 A | | 9/2000 | Shehada et al. |
| 6,233,047 B1* | | 5/2001 | Jung ............... G01J 3/0218 356/600 |
| 6,255,118 B1 | | 7/2001 | Alfano et al. |
| 6,885,440 B2 | | 4/2005 | Silcott et al. |
| 7,015,484 B2 | | 3/2006 | Gillispie et al. |
| 7,086,279 B2 | | 8/2006 | Gilby et al. |
| 7,129,505 B2 | | 10/2006 | Oostman, Jr. et al. |
| 7,154,595 B2 | | 12/2006 | Paldus et al. |
| 7,470,917 B1* | | 12/2008 | Hoang .............. G01N 21/645 250/458.1 |
| 7,578,973 B2 | | 8/2009 | Call et al. |
| 8,269,192 B2 | | 9/2012 | Dixon |
| 8,729,502 B1 | | 5/2014 | Klotzkin |
| 8,802,007 B2 | | 8/2014 | Kaiga et al. |
| 8,859,990 B2 | | 10/2014 | Ng et al. |
| 8,901,513 B2 | | 12/2014 | Gilmore et al. |
| 8,987,685 B2 | | 3/2015 | Fawcett et al. |
| 9,040,307 B2 | | 5/2015 | Reed et al. |
| 9,068,947 B2 | | 6/2015 | Fawcett et al. |
| 2003/0048445 A1* | | 3/2003 | Tokhtuev ........... G01N 33/1886 356/411 |
| 2004/0106164 A1 | | 6/2004 | Brown et al. |
| 2005/0070005 A1 | | 3/2005 | Keller |
| 2007/0064228 A1* | | 3/2007 | Tartakovsky ............. G01J 3/10 356/317 |
| 2009/0101842 A1* | | 4/2009 | Shepard ............ G01N 21/6402 250/484.4 |
| 2012/0208264 A1 | | 8/2012 | Bernd et al. |
| 2012/0228519 A1 | | 9/2012 | Gilmore et al. |
| 2013/0233796 A1 | | 9/2013 | Rao et al. |
| 2013/0327961 A1* | | 12/2013 | Tedetti ............... G01N 21/6486 250/206 |
| 2014/0264077 A1 | | 9/2014 | Tokhtuev et al. |
| 2015/0005186 A1 | | 1/2015 | Huang |
| 2015/0044098 A1 | | 2/2015 | Smart et al. |
| 2015/0090900 A1 | | 4/2015 | Banks et al. |
| 2015/0211043 A1 | | 6/2015 | Ram et al. |
| 2016/0123882 A1 | | 5/2016 | Gilmore et al. |

FOREIGN PATENT DOCUMENTS

| | | |
|---|---|---|
| WO | 03023379 A1 | 3/2003 |
| WO | 2005/008198 A2 | 1/2005 |

OTHER PUBLICATIONS

Baker, Fluorescence Excitation-Emission Matrix Characterization of Some Sewage-Impacted Rivers, Jan. 26, 2001, Environmental Science & Technology, vol. 35, No. 5 (Year: 2001).*
Roberto Barbini, et al, Enea Fluorosensor System Used in Monitoring the Adriatic Sea, Proceedings of Spie, vol. 2959, Jan. 17, 1997, pp. 254-264, printed Nov. 29, 2016. https://www.spiedigitallibrary.org/conference-proceedings-of-spie.
English language translation of CN103245644A.
Palmer, Stephanie C. J. et al., "Ultraviolet Fluorescence LiDAR (UFL) as a Measurement Tool for Water Quality Parameters in Turbid Lake Conditions," Remote Sensing, vol. 5, issue 9, Sep. 11, 2013, pp. 4405-4422.
Henderson, R. K. et al., "Fluorescence as a potential monitoring tool for recycled water systems: A review," Water Research 43 (2009), Dec. 3, 2008, pp. 863-881.
"Fluorescence Spectometers-FluoTime 200" product information (9 pages), Accessed online on Aug. 2015.
Baker, Andy, Abstract of "Fluorescence Excitation-Emission Matrix Characterization of Some Sewage-Impacted Rivers," Environmental Science & Technology, Jan. 26, 2001 (2 pages).

* cited by examiner

Figure 1: Sensor Body

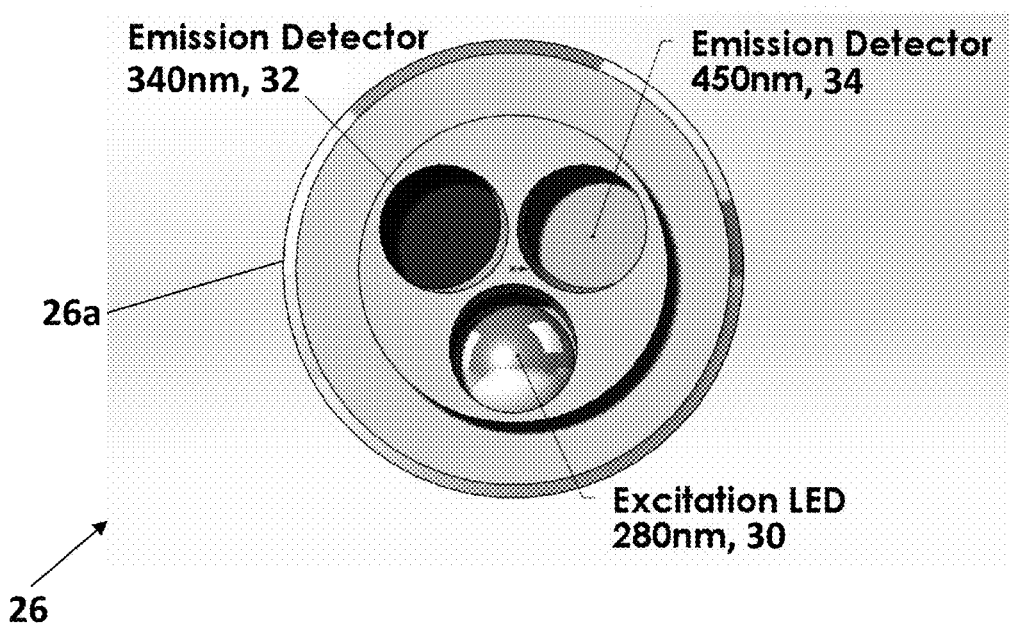
Figure 2A: Front View, Opto-Mechanical Head
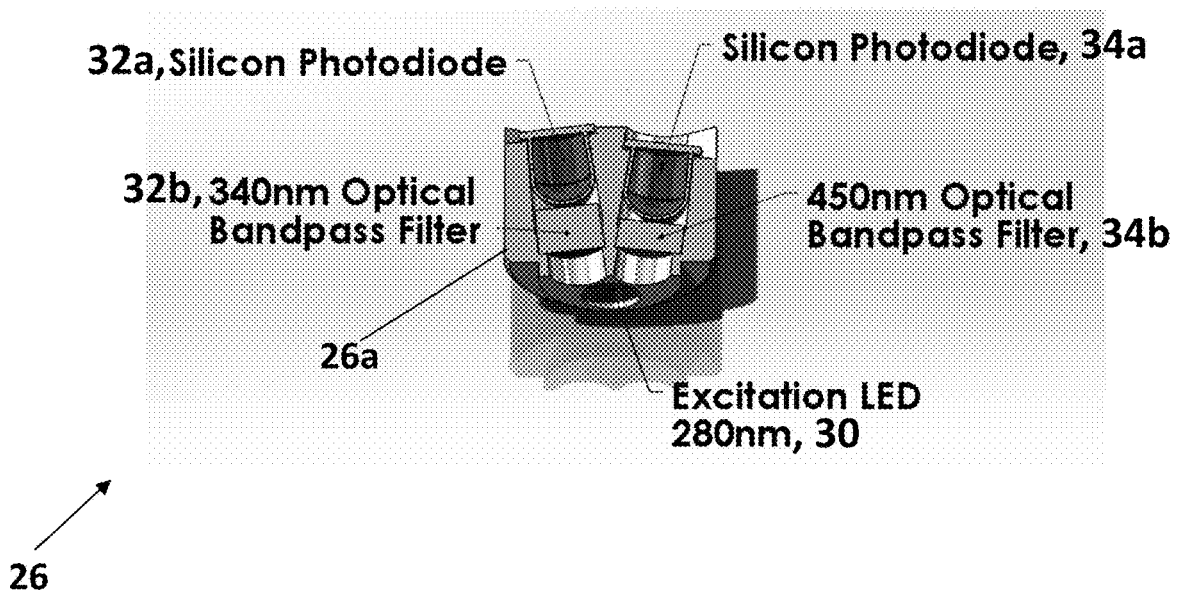
Figure 2B: Opto-Mechanical Head
Figure 2

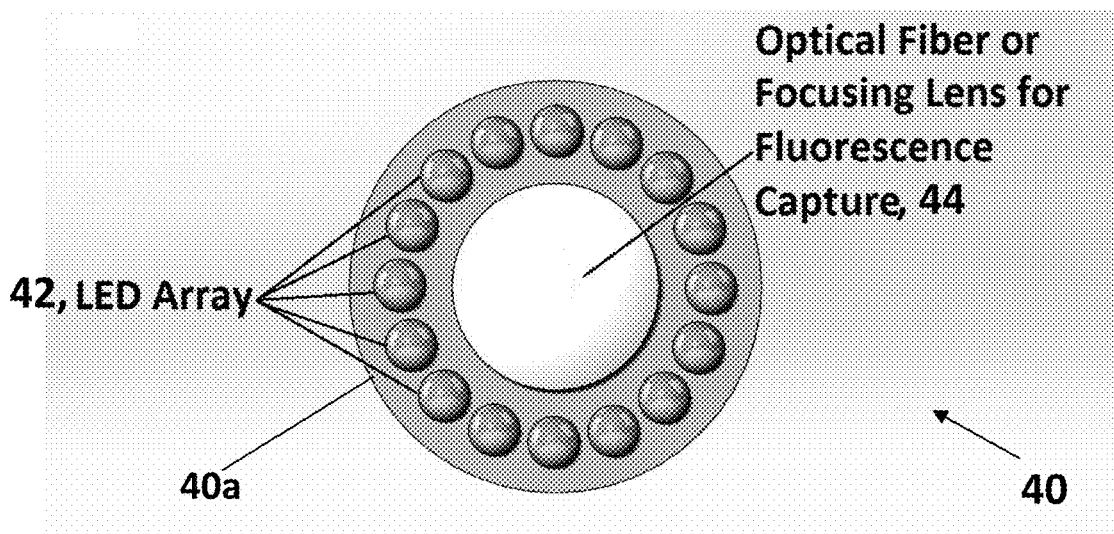
Figure 3A: Opto-Mechanical Head for Multiparameter Sensing (Front View)
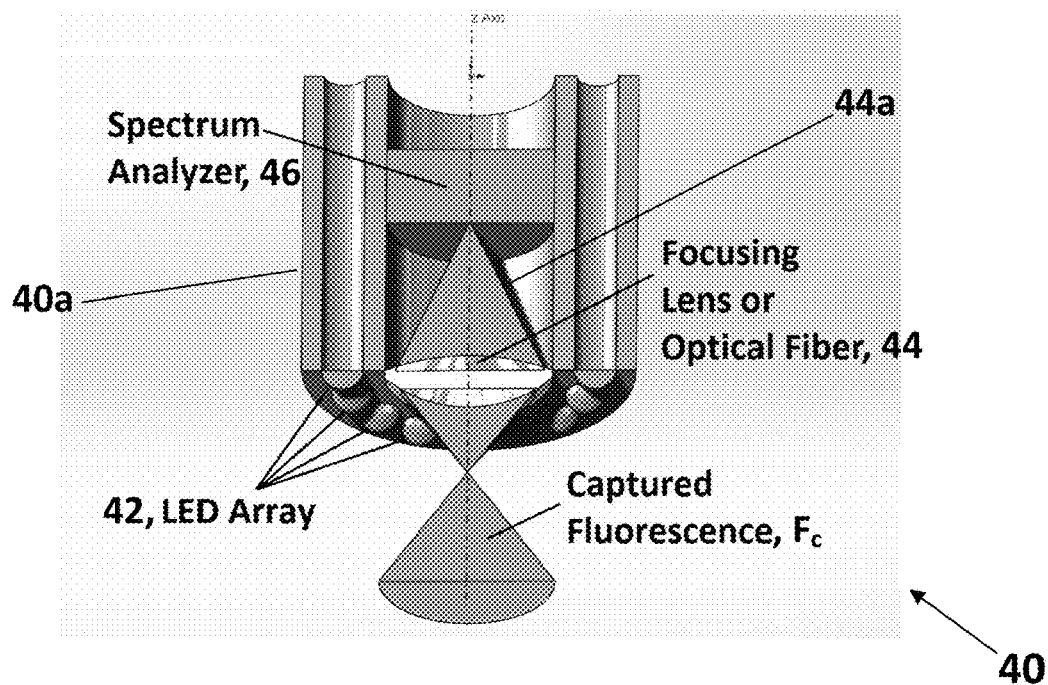
Figure 3B: Opto-Mechanical Head for Multiparameter Sensing (Cutaway View)
Figure 3

Apparatus 10 (e.g., a sensor body like a Sonde)

Array of excitation sources 30 configured to provide respective excitation source optical signaling at a respective illuminating wavelength.

Multiple emission detectors 32, 34 configured to detect multiple emission wavelengths emitted from water containing information about multiple coexisting fluorescent species present in the water that emit optical radiation at at least two different wavelengths when illuminated by the respective illuminating wavelength provided from the array of excitation sources, and provide multiple emission detector signaling containing information about the multiple coexisting fluorescent species.

Signal processor or processing module 100 configured at least to:

receive signaling containing information about the excitation source signaling provided by the array of excitation sources 30, and the multiple emission detector signaling provided by the multiple emission detectors 32, 34;

determine corresponding signaling containing information about an identification of the multiple coexisting fluorescent species present in the water using the near-simultaneous identification technique; based upon the signaling received; and/or provide the corresponding signaling containing information about an identification of the multiple coexisting fluorescent species present in the water using the near-simultaneous identification technique.

Other signal processor circuits or components 102 that do not form part of the underlying invention, e.g., including input/output modules, one or more memory modules, data, address and control busing architecture, etc.

Figure 4

MULTI EXCITATION-MULTI EMISSION FLUOROMETER FOR MULTIPARAMETER WATER QUALITY MONITORING

CROSS-REFERENCE TO RELATED APPLICATIONS

This application claims benefit to, and is a continuation application of, parent patent application Ser. No. 15,226,407, filed 2 Aug. 2016, which claims benefit to provisional patent application Ser. No. 62/200,336, filed 3 Aug. 2015; which are both incorporated by reference in their entirety.

BACKGROUND OF THE INVENTION

1. Field of Invention

This invention relates to a technique for determining the quality of water; and more particularly relates to a technique for determining the quality of water based upon the detection of multiple coexisting fluorescent species present in the water.

2. Description of Related Art

Techniques for monitoring water are known in the art, including monitoring for the presence of sewage and waste water. A confirmation of sewage impacted water is a complicated process, e.g., especially when using a single emission wavelength alone, which has been found to not unambiguously determine the presence waste water. In view of this, there is a need in the industry for a better way for monitoring water.

SUMMARY OF THE INVENTION

By way of example, the present invention includes new and unique techniques for monitoring the quality of water.

According to some embodiments, the present invention may include apparatus, e.g., in the form of a fluorometer, for monitoring the quality of water, featuring a combination of an array of excitation sources, an array of multiple emission detectors and a signal processor or processing module.

Each excitation source In the array of excitation sources may be configured to provide respective excitation source optical signaling at a respective illuminating wavelength, e.g., in relation to the water being monitored.

The array of multiple emission detectors may be configured to detect multiple emission wavelengths emitted from the water containing information about multiple coexisting fluorescent species present in the water that emit optical radiation at at least two different wavelengths when illuminated by the respective illuminating wavelength provided from the array of excitation sources, and provide multiple emission detector signaling containing information about the multiple coexisting fluorescent species.

The signal processor or processing module may be configured to receive the multiple emission detector signaling, and determine corresponding signaling containing information about an identification of the multiple coexisting fluorescent species present in the water using a near-simultaneous identification technique, based upon the multiple emission detector signaling received.

The apparatus may include one or more of the following additional features:

The array of excitation sources may include an excitation source, e.g., an excitation LED, and the illuminating wavelength may be 280 nanometers; and the array of multiple emission detectors may include a first emission detector configured to detect the optical radiation at 340 nanometers for detecting the presence of peak-T, protein-like (e.g., including peak T-tryptophan) in the water; and a second emission detector configured to detect the optical radiation at 450 nanometers for detecting the present of peak A humic/fulvic-like in the water.

The array of multiple emission detectors may include a plurality of photodiodes and optical bandpass filters configured to sense and filter the multiple emission wavelengths emitted from water, and provide the multiple emission detector signaling.

The optical bandpass filters may include, e.g., a first photodiode and optical bandpass filter configured to filter the optical radiation at 340 nanometers for detecting the present of peak-T, protein-like in the water; and a second photodiode and optical bandpass filter configured to filter the optical radiation at 450 nanometers for detecting the present of peak A humic/fulvic-like in the water.

The array of excitation sources may include a plurality of excitation sources configured to provide a plurality of excitation source optical signaling at a plurality of illuminating wavelengths, e.g., such as plurality of excitation LEDs.

The array of multiple emission detectors may include optical bandpass filters spectrally centered about fluorescence emission wavelengths of interest.

The array of multiple emission detectors may include a combination of one or more optical fibers or focusing lens and an optical spectrum analyzer for fluorescence capture and analysis.

The plurality of excitation sources may be configured to respond to suitable control signaling and near-simultaneously provide the plurality of excitation source optical signaling to produce the plurality of illuminating wavelengths and detect the multiple emission wavelengths. Alternatively, the plurality of excitation sources may be configured to respond to corresponding suitable control signaling and selectively provide the plurality of excitation source optical signaling to produce the plurality of illuminating wavelengths and detect the multiple emission wavelengths. In other words, the plurality of excitation sources and the array of multiple emission detectors may be configured to respond to control signaling and either near-simultaneously or selectively provide the plurality of excitation source optical signaling to produce any combination of excitation wavelengths or detected fluorescence emission.

The fluorometer may be configured in, or forms part of, a single sensor body. The single sensor body may include, or take the form of, a sonde having a water tight housing that encloses the fluorometer. The sonde may include a port; and the fluorometer may include an electrical connector configured to plug into the port of the sonde. The electrical connector may be configured to attach to a printed circuit board (PCB), e.g., containing sensor electronics. The sensor electronics may include the signal processor or processing module. The fluorometer may include an opto-mechanical head that contains electro-opto-mechanical components, including the array of excitation sources and the array of multiple emission detectors. The water tight housing may include a window configured to allow optical transmission/interaction between the multiple coexisting fluorescent species to be measured in the water being monitored and the electro-opto-mechanical components contained in the sonde. By way of example, the window may be made of Sapphire, as well as multiple other window materials.

By way of example, the signal processor or processing module may be configured to provide the corresponding signaling containing information about the identification of the multiple coexisting fluorescent species present in the water using the near-simultaneous identification technique for further processing. By way of example, the further processing may include, or take the form of, providing control signaling for further processing the water being monitored; or the further processing may include providing the control signaling for adapting the water monitoring process itself for monitoring the water. By way of further example, the corresponding signaling may include information to provide a visual display related to the identification, and/or an audio/visual alarm, etc.

The fluorometer may include an opto-mechanical head configured with electro-opto-mechanical components, including the array of excitation sources and the array of multiple emission detectors.

The plurality of excitation sources may be configured or arranged circumferentially about the array of multiple emission detectors.

According to some embodiments, the present invention may include apparatus taking the form of a signal processor or processing module configured at least to:

receive signaling containing information about excitation source signaling provided by an array of excitation sources, each excitation source configured to provide respective excitation source optical signaling at a respective illuminating wavelength, and multiple emission detector signaling provided by an array of multiple emission detectors configured to detect multiple emission wavelengths emitted from water containing information about multiple coexisting fluorescent species present in the water that emit optical radiation at at least two different wavelengths when illuminated by the respective illuminating wavelength provided from the array of excitation sources, the multiple emission detector signaling containing information about the multiple coexisting fluorescent species; and determine corresponding signaling containing information about an identification of the multiple coexisting fluorescent species present in the water using a near-simultaneous identification technique, based upon the signaling received.

By way of example, the signal processor or signal processor module may take the form of some combination of a signal processor and at least one memory including a computer program code, where the signal processor and at least one memory are configured to cause the apparatus to implement the functionality of the present invention, e.g., to respond to signaling received and to determine the corresponding signaling, based upon the signaling received. Moreover, such apparatus may also include one or more of the features set forth above.

According to some embodiments, the present invention may include a method comprising steps for receiving in a signal processor or processing module signaling containing information about excitation source signaling provided by an array of excitation sources, each excitation source configured to provide respective excitation source optical signaling at a respective illuminating wavelength, and multiple emission detector signaling provided by an array of multiple emission detectors configured to detect multiple emission wavelengths emitted from water containing information about multiple coexisting fluorescent species present in the water that emit optical radiation at at least two different wavelengths when illuminated by the respective illuminating wavelength provided from the array of excitation sources, the multiple emission detector signaling containing information about the multiple coexisting fluorescent species; and determining in the signal processor or processing module corresponding signaling containing information about an identification of the multiple coexisting fluorescent species present in the water using the near-simultaneous identification technique, based upon the signaling received.

The method may also include one or more of the features set forth above.

According to some embodiments, the present invention may include apparatus taking the form of means for receiving in a signal processor or processing module signaling containing information about excitation source signaling provided by an array of excitation sources, each excitation source configured to provide respective excitation source optical signaling at a respective illuminating wavelength, and multiple emission detector signaling provided by an array of multiple emission detectors configured to detect multiple emission wavelengths emitted from water containing information about multiple coexisting fluorescent species present in the water that emit optical radiation at at least two different wavelengths when illuminated by the respective illuminating wavelength provided from the array of excitation sources, the multiple emission detector signaling containing information about the multiple coexisting fluorescent species; and means for determining in the signal processor or processing module corresponding signaling containing information about an identification of the multiple coexisting fluorescent species present in the water using the near-simultaneous identification technique, based upon the signaling received.

Such apparatus may also include one or more of the features set forth above.

According to some embodiments of the present invention, the apparatus may also take the form of a computer-readable storage medium having computer-executable components for performing the steps of the aforementioned method. The computer-readable storage medium may also include one or more of the features set forth above.

At the time of the instant patent application filing, others similar products are known and made by companies like Turner Designs and UviLux Tryptophan Fluorometer.

Similarities between the present invention and these known products may include: Fluorescence-based optical sensing of wastewater, emission wavelength for Tryptophan will overlap with only one of the emission wavelengths set forth herein.

Differences between the present invention and these known products may include: The sensor set forth herein according to the present invention has a key advantage and innovation of utilizing dual emission wavelengths for meaningful and increased confidence of detection of wastewater—all in a single sensing body.

BRIEF DESCRIPTION OF THE DRAWING

The drawing includes FIGS. 1-4, which are not necessarily drawn to scale, as follows:

FIG. 2 includes FIGS. 2A and 2B, where FIG. 2A is a front view of an opto-mechanical head that may form part of the sensor body in FIG. 1, and where FIG. 2B is a cross-sectional (or cutaway) view of the opto-mechanical head in FIG. 2A, according to some embodiments of the present invention.

FIG. 3 includes FIGS. 3A and 3B, where FIG. 3A is a front view of an opto-mechanical head for multiple parameter sensing that may form part of the sensor body in FIG. 1, and where FIG. 3B is a cross-sectional view of the opto-mechanical head in FIG. 3A, according to some embodiments of the present invention.

FIG. 4 shows a block diagram of apparatus, e.g., having a signal processor or signal processing module for implementing signal processing functionality, according to some embodiments of the present invention.

DETAILED DESCRIPTION OF BEST MODE OF THE INVENTION

The Underlying Technique in General

Figure 1:
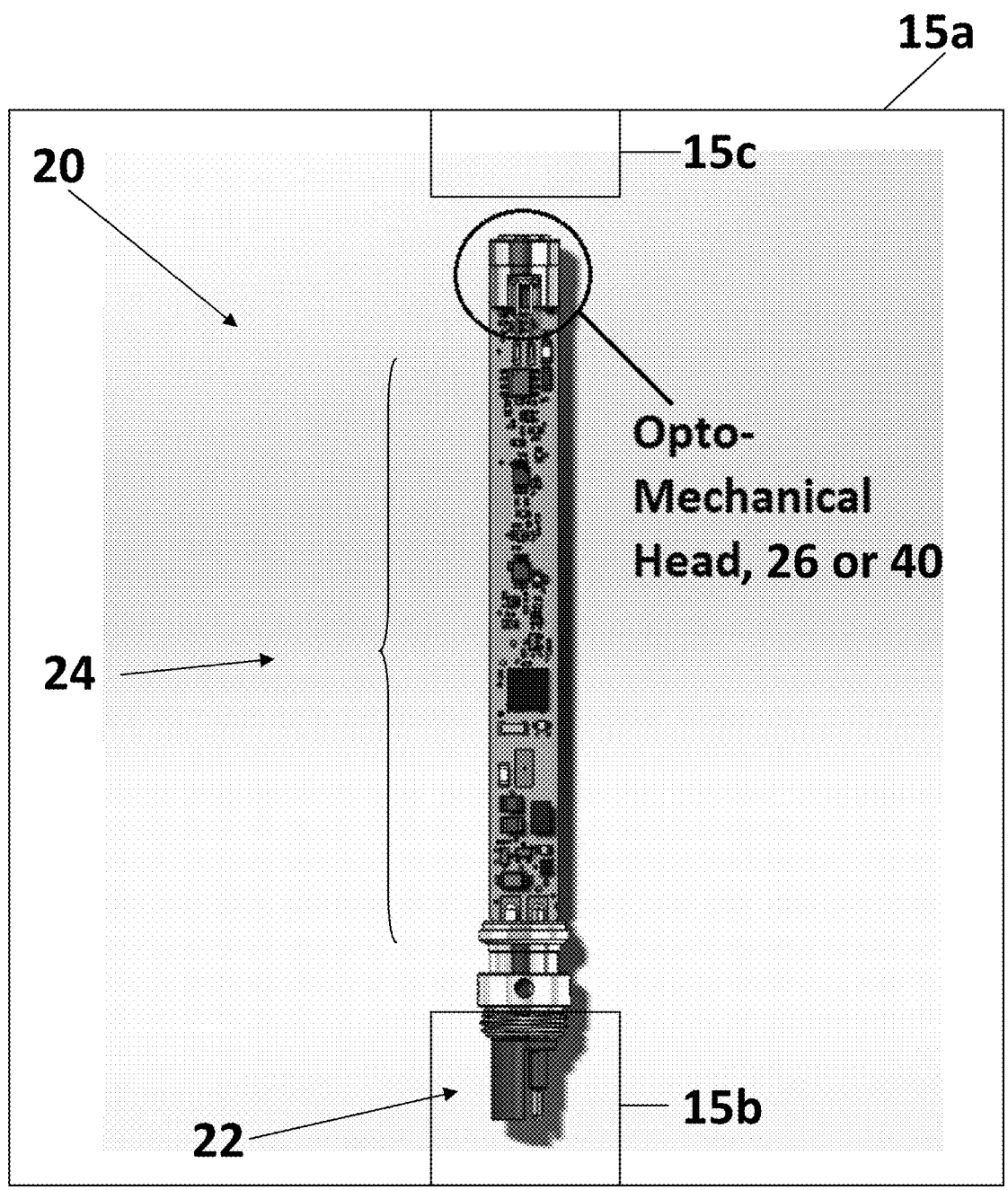
FIG. 1 shows a diagram of apparatus in the form of a sensor body, according to some embodiments of the present invention.

In its first incarnation, a fluorometer generally indicated as 20 according to the present invention may be configured to measure fluorescence of peak T-tryptophan-like ($\lambda_{ex/em}$=280/340 nm) and peak A humic/fulvic-like ($\lambda_{ex/em}$=280/450 nm), e.g., using a single excitation source/dual emission detection as means of identifying sewage impacted water in general. The affirmative confirmation of sewage impacted water is complicated in that it may be more accurately determined through near-simultaneous identification of multiple fluorescence species. For the particular case at hand, and according to some embodiments of the present invention, one may seek to near-simultaneously identify two species requiring two detected fluorescence emission wavelengths within a single sensing body. It is the combined information of multiple fluorescence that serves to address the single issue of wastewater identification. The inventors have come to understand that a single emission wavelength alone cannot unambiguously determine the presence of wastewater, and provide new and unique techniques disclosed herein to solve this "single emission wavelength" problem in the art.

Moreover, the spirit of the present invention is not intended to be restricted to the identification of only two fluorescence species, but rather is intended to encompass the possibility of near-simultaneous detection of multiple fluorescence species, e.g., including three or more fluorescence species. According to some embodiments, this notion can be extended to include multiple excitation sources and multiple emission wavelength detection to near-simultaneously detect multiple fluorescence species within a single sensing body. For water quality monitoring, it is often the case that the presence of multiple fluorescence species tends to obscure or interfere with any particular desired measurand. The near-simultaneous identification of the multiple species disclosed or presented herein serves to isolate and more singly describe/identify the water quality parameter of interest.

FIGS. 1-3

FIGS. 1 and 2 shows a first embodiment, based upon one seeking to near-simultaneously identify two species requiring two detected fluorescence emission wavelengths within a single sensing body, e.g., which may take the form of apparatus 10 generally shown in FIG. 1 having a fluorometer 20 with an opto-mechanical head 26 shown in detail in FIG. 2. This notion can be extended to include multiple excitation sources and multiple emission wavelength detection to near-simultaneously detect multiple fluorescence species within a single sensing body using an opto-mechanical head 40, e.g. consistent with that disclosed in relation to FIG. 3.

The implementations of the sensor body 10 and the fluorometers 20 differ primarily in the details concerning the opto-mechanical heads 26 and 40 shown in FIGS. 2 and 3. Embodiments of the sensor body 10 disclosed in this patent application have at least the following in common: The sensor body 10 generally includes, or consists of, a water tight housing 15a (FIG. 1) that encloses the fluorometer 20 and has at least part of an electrical connector 22 that plugs into a port 15b on the sensor body 10. The sensor body 10 may include, or take the form of, a Sonde structure. The fluorometer 20 may be configured with a printed circuit board (PCB) generally indicated as 24, and the electrical connector 22 may also be attached to the printed circuit board (PCB) 24 containing the sensor electronics, e.g., which may include a signal processor or processing module 100 (FIG. 4), e.g., for implementing signal processing functionality consistent with that disclosed herein. The fluorometer 20 may be configured with the opto-mechanical head 26 or 40, which may be attached to the PCB 24. The opto-mechanical head 26 or 40 may contain the electro-opto-mechanical components, e.g., including light emitting diodes (LEDs) 30 and emission detectors 32, 34 having photodetectors or photodiodes (PDs) 32a, 34a and optical bandpass filters 32b, 34b. One end/side of the water tight housing 15a may also contain a window 15c (FIG. 1) that may be configured to allow optical transmission/interaction between the fluorophore (i.e., fluorescent species to be measured) and the optical sensing components 30, 32 and 34 in relation to the embodiment in FIG. 2, or LED array 42 or focusing lens or optical fiber 44 in relation to the embodiment in FIG. 3. By way of example, the window may be made of Sapphire, although the scope of the invention is not intended to be limited to the same. Embodiments are envisioned using other types or kind of window material either now known or later developed in the art, e.g., as one skilled in the art would be appreciate.

In particular, FIG. 1 shows or depicts the sensor body 10 with the electrical connector 22 at its bottom, the PCB 24 (e.g., shown in FIG. 1 as an electrically populated circuit board in the main part of the sensor body 10), and the opto-mechanical head 26 or 40 (as circled in FIG. 1), e.g., containing the LEDs 30 (FIG. 2), PDs and optical bandpass filters 32, 34 as disclosed in relation to FIG. 2. In FIG. 1, the sensor body 10 is shown by way of example as a representation of a typical sensor body and is not intended to be accurate in scale or engineering detail per se. One of the essential components which differentiates all of the disclosed embodiments herein is the opto-mechanical head 26 or 40 (as circled in FIG. 1). In view of this, and to that end, FIGS. 2A, 2B, 3A and 3B show only details associated with the opto-mechanical head 26 or 40.

FIG. 2: Example of Particular Embodiment

FIGS. 2A and 2B show a first embodiment of the opto-mechanical head 26 that can form part of the sensor body 10 (FIG. 1), according to some embodiments of the present invention. By way of example, the opto-mechanical head 26 includes an opto-mechanical head body 26a that may contain a single LED 30 at an excitation wavelength of 280 nm, and two emission detectors 32, 34. By way of example, the two emission detectors 32, 34 may include two Silicon or other suitable photodetectors 32a, 34a with respective optical bandpass fitters 32b, 34b spectrally centered at 340 nm and 450 nm. This opto-mechanical configuration is designed to detect two coexisting fluorescent species that emit optical radiation at 340 nm and 450 nm respectively when illuminated by the 280 nm optical source 30. By way of example, the photodiodes 32a, 34a and the LED 30 may be configured, or may employ, a ball lens configuration to maximize fluorescence collection, e.g., consistent with that shown in FIGS. 2A and 2B.

FIG. 3: Example of Generalized Embodiment

FIGS. 3A and 3B show a second, more generalized, embodiment having the opto-mechanical head 40 having an opto-mechanical head body 40a that can form part of the sensor 10 (FIG. 1), according to some embodiments of the present invention. By way of example, the opto-mechanical head 40 may contain an array 42 of many excitation LEDs. In FIG. 3A, the array 42 is shown having 16 excitation LEDs, although the scope of the invention is not intended to be limited to any particular number of excitation LEDs. The excitation wavelengths and number of LEDs can be chosen to suit the desired application. For example, depending on the particular application a different number of excitation LEDs may be used. In operation, each excitation LED is configured to provide respective excitation LED optical signaling at a respective illuminating wavelength, e.g., consistent with that set forth herein. Moreover, the opto-mechanical head 40 may include receiving optics 44, e.g., such as either an array of photodiodes with associated optical bandpass filters spectrally centered about fluorescence emission wavelengths of interest, or alternatively, such as an optical spectrum analyzer 46 as shown (FIG. 3B). Both of these receiving optics techniques serve as a means to spectrally discriminate the collected/captured fluorescence optical signaling generally indicated as $F_e$. The fluorescence can be captured either through a focusing lens 44 (FIG. 3B) that provides focusing lens optical signaling 44a onto a spectrum analyzer 46, or by using one or more fiber optic waveguides, e.g., including a bundle of optical fibers (also indicated by reference label 44). The opto-mechanical head 40 may be configured or designed to detect multiple, independent or coexisting fluorescent species that emit optical radiation in a range or distribution of emission wavelengths when illuminated by the LED array 42. The array of LEDs 42 and photodiodes (or the spectrum analyzer 46) need not be near-simultaneously activated, but can be selectively enabled or scanned to produce any combination of excitation wavelengths or detected fluorescence emission.

In FIG. 4, the plurality of LED excitation sources 42 may be configured or arranged circumferentially about the array of multiple emission detectors 44.

FIG. 4: Implementation of Signal Processing Functionality

By way of further example, FIG. 4 shows the apparatus or sensor body 10 according to some embodiments of the present invention for implementing the associated signal processing functionality. The apparatus or sensor body 10 may include a signal processor or processing module 100 configured at least to:

receive signaling containing information about excitation source signaling provided by an array of excitation sources, each excitation source configured to provide respective excitation source optical signaling at a respective illuminating wavelength, and multiple emission detector signaling provided by an array of multiple emission detectors configured to detect multiple emission wavelengths emitted from water containing information about multiple coexisting fluorescent species present in the water that emit optical radiation at at least two different wavelengths when illuminated by the respective illuminating wavelength provided from the array of excitation sources, the multiple emission detector signaling containing information about the multiple coexisting fluorescent species; and determine corresponding signaling containing information about an identification of the multiple coexisting fluorescent species present in the water using a near-simultaneous identification technique, based upon the signaling received.

In operation, the signal processor or processing module 100 may be configured to provide the corresponding signaling containing information about the identification of the multiple coexisting fluorescent species present in the water using the near-simultaneous identification technique, e.g., for further processing, consistent with that set forth herein. The scope of the invention is not intended to be limited to any particular type, kind or manner of further processing, and may include further processing techniques either now known or later developed in the future.

The signal processor or processing module 100 may be configured in, or form part of, a sensor body, e.g., like a sonde.

By way of example, the functionality of the signal processor or processing module 100 may be implemented using hardware, software, firmware, or a combination thereof. In a typical software implementation, the signal processor or processing module 100 would include one or more microprocessor-based architectures having, e.g., at least one signal processor or microprocessor like element 100. One skilled in the art would be able to program with suitable program code such a microcontroller-based, or microprocessor-based, implementation to perform the signal processing functionality disclosed herein without undue experimentation. For example, the signal processor or processing module 100 may be configured, e.g., by one skilled in the art without undue experimentation, to receive the signaling containing information about excitation source signaling provided by an array of excitation sources, each excitation source configured to provide respective excitation source optical signaling at a respective illuminating wavelength, and multiple emission detector signaling provided by multiple emission detectors configured to detect multiple emission wavelengths emitted from water containing information about multiple coexisting fluorescent species present in the water that emit optical radiation at at least two different wavelengths when illuminated by the respective illuminating wavelength provided from the array of excitation sources, the multiple emission detector signaling containing information about the multiple coexisting fluorescent species, consistent with that disclosed herein.

Moreover, the signal processor or processing module 100 may be configured, e.g., by one skilled in the art without undue experimentation, to determine the corresponding signaling containing information about an identification of the multiple coexisting fluorescent species present in the water using a near-simultaneous identification technique, consistent with that disclosed herein. By way of example, the scope of the invention is not intended to be limited to any particular type or kind of signal processing implementation and/or technique for the near-simultaneous identification of the multiple coexisting fluorescent species present in the water. The scope of the invention is intended to include signal processing implementations and/or techniques for the near-simultaneous identification of the multiple coexisting fluorescent species present in the water that are both now known or later developed in the future, as would be understood and appreciate by one skilled in the art.

The scope of the invention is not intended to be limited to any particular implementation using technology either now known or later developed in the future. The scope of the invention is intended to include implementing the functionality of the signal processor(s) 100 as stand-alone processor, signal processor, or signal processor module, as well as separate processor or processor modules, as well as some combination thereof.

The signal processor or processing module 10 may also include, e.g., other signal processor circuits or components 102, including random access memory or memory module (RAM) and/or read only memory (ROM), input/output devices and control, and data and address buses connecting the same, and/or at least one input processor and at least one output processor, e.g., which would be appreciate by one skilled in the art.

The Optical Components

By way of example, and as one skilled in the art would appreciate, optical components like LEDs, photodiodes, optical bandpass filters, optical fiber or fibers, LED arrays, focusing lens, optical spectrum analyzers are all known in the art, and the scope of the invention is not intended to be limited to any particular type or kind thereof that may be used herein. The scope of the invention is intended to include using such optical components that may be now known in the art or later developed in the future.

The Scope of the Invention

While the invention has been described with reference to an exemplary embodiment, it will be understood by those skilled in the art that various changes may be made and equivalents may be substituted for elements thereof without departing from the scope of the invention. In addition, may modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. A single body sensor for monitoring the quality of water, comprising:
   a watertight housing configured to enclose a fluorometer; and
   the fluorometer having
      excitation sources, each excitation source configured to provide respective excitation source optical signaling at a respective illuminating wavelength;
      optics configured to receive optical radiation in a range or distribution of emission wavelengths, and provide collected or captured fluorescence optical signaling containing information about multiple, independent or coexisting fluorescent species in water that emit the optical radiation in the range or distribution of the emission wavelengths when illuminated by the excitation sources; and
      a spectrum analyzer configured to receive the collected or captured fluorescence optical signaling, spectrally discriminate the collected or captured fluorescence optical signaling received to determine information about the multiple, independent or coexisting fluorescent species in the water, and provide spectrum analyzer signaling containing information about whether the water is impacted by sewage determined by an identification based upon the multiple, independent or coexisting fluorescent species detected in the water.

2. A single body sensor according to claim 1, wherein the excitation sources comprise a plurality of excitation LEDs configured to provide respective LED excitation source optical signaling at a corresponding plurality of respective illuminating wavelengths.

3. A single body sensor according to claim 2, wherein the plurality of excitation LEDs are configured or arranged circumferentially about the optics and the spectrum analyzer.

4. A single body sensor according to claim 1, wherein the optics comprise a focusing lens that provides the collected or captured fluorescence optical signaling in the form of focusing lens signaling onto the spectrum analyzer.

5. A single body sensor according to claim 1, wherein the optics comprise one or more fiber optic waveguides that provides the collected or captured fluorescence optical signaling in the form of fiber optic waveguide signaling onto the spectrum analyzer.

6. A single body sensor according to claim 1, wherein the spectrum analyzer is selectively enabled or scanned to produce any combination of excitation wavelengths or detected fluorescence emission.

7. A single body sensor according to claim 1, wherein the fluorometer comprises an opto-mechanical head that contains the excitation sources, the optics and the spectrum analyzer.

8. A single body sensor according to claim 1, wherein the optics comprises photodiodes with associated bandpass filters spectrally centered about fluorescence emission wavelengths of interest.

9. A single body sensor according to claim 1, wherein the single body sensor comprises a sonde having the watertight housing that encloses the fluorometer.

10. A single body sensor according to claim 9, wherein the sonde comprises a port; and the fluorometer comprises an electrical connector configured to plug into the port of the sonde.

11. A single body sensor according to claim 10, wherein the electrical connector is configured to attach to a printed circuit board containing sensor electronics.

12. A single body sensor according to claim 11, wherein the sensor electronics include the signal processor or processing module.

13. A single body sensor according to claim 12, wherein the water tight housing has a window configured to allow optical transmission/interaction between the multiple, independent or coexisting fluorescent species to be detected and the excitation sources and the optics, including where the window is made of Sapphire.

14. A single body sensor according to claim 12, wherein the spectrum analyzer comprises a signal processor or processing module configured to receive the collected or captured fluorescence optical signaling, spectrally discriminate the collected or captured fluorescence optical signaling received to determine information about the multiple, independent or coexisting fluorescent species in the water, and provide spectrum analyzer signaling containing information about sewage impacted water determined by a wastewater identification based upon the multiple, independent or coexisting fluorescent species detected in the water.

15. A method for monitoring the quality of water with a fluorometer, comprising:
configuring a single body sensor with a watertight housing that encloses a fluorometer;
configuring the fluorometer with excitation sources, and providing from each excitation source respective excitation source optical signaling at a respective illuminating wavelength;
configuring the fluorometer with optics, receiving with the optics optical radiation in a range or distribution of emission wavelengths, and providing from the optics collected or captured fluorescence optical signaling containing information about multiple, independent or coexisting fluorescent species in water that the emit optical radiation in the range or distribution of the emission wavelengths when illuminated by the excitation sources; and
configuring the fluorometer with a spectrum analyzer, receiving with the spectrum analyzer the collected or captured fluorescence optical signaling, spectrally discriminating with the spectrum analyzer the collected or captured fluorescence optical signaling received to determine information about the multiple, independent or coexisting fluorescent species in the water, and provide spectrum analyzer signaling containing information about whether the water is impacted by sewage determined by an identification based upon the multiple, independent or coexisting fluorescent species detected in the water.

16. A method according to claim 15, wherein the method comprises configuring the excitation sources with a plurality of excitation LEDs that provide respective LED excitation source optical signaling at a corresponding plurality of respective illuminating wavelengths.

17. A method according to claim 16, wherein the method comprises arranging circumferentially the plurality of excitation LEDs about the optics and the spectrum analyzer.

18. A method according to claim 15, wherein the method comprises configuring the optics with a focusing lens that provides the collected or captured fluorescence optical signaling in the form of focusing lens signaling onto the spectrum analyzer.

19. A method according to claim 15, wherein the method comprises configuring the optics with one or more fiber optic waveguides that provides the collected or captured fluorescence optical signaling in the form of fiber optic waveguide signaling onto the spectrum analyzer.

20. A method according to claim 15, wherein the method comprises selectively enabling or scanning the spectrum analyzer to produce any combination of excitation wavelengths or detected fluorescence emission.

21. A method according to claim 15, wherein the method comprises configuring the spectrum analyzer with a signal processor or processing module that receives the collected or captured fluorescence optical signaling, spectrally discriminates the collected or captured fluorescence optical signaling received to determine information about the multiple, independent or coexisting fluorescent species in the water, and provide spectrum analyzer signaling containing information about sewage impacted water determined by a wastewater identification based upon the multiple, independent or coexisting fluorescent species detected in the water.

22. A sonde for monitoring the quality of water, comprising:
a watertight housing configured to enclose a fluorometer; and
the fluorometer having an opto-mechanical head that contains excitation LED sources, optics and a spectrum analyzer,
each excitation LED source configured to provide respective excitation source optical signaling at a respective illuminating wavelength;
the optics having photodiodes and associated bandpass filters spectrally centered about fluorescence emission wavelengths of interest, and being configured to receive optical radiation in a range or distribution of emission wavelengths, and provide collected or captured fluorescence optical signaling containing information about multiple, independent or coexisting fluorescent species in water that emit the optical radiation in the range or distribution of the emission wavelengths when illuminated by the excitation sources; and
the spectrum analyzer being selectively enabled or scanned to produce any combination of excitation wavelengths or detected fluorescence emission, and configured to receive the collected or captured fluorescence optical signaling, spectrally discriminate the collected or captured fluorescence optical signaling received to determine information about the multiple, independent or coexisting fluorescent species in the water, and provide spectrum analyzer signaling containing information about whether the water is impacted by sewage determined by an identification based upon the multiple, independent or coexisting fluorescent species detected in the water.

* * * * *